United States Patent
Dang et al.

(10) Patent No.: US 7,208,551 B2
(45) Date of Patent: Apr. 24, 2007

(54) POLYARYLENEETHERKETONE PHOSPHINE OXIDE COMPOSITIONS INCORPORATING CYCLOALIPHATIC UNITS FOR USE AS POLYMERIC BINDERS IN THERMAL CONTROL COATINGS AND METHOD FOR SYNTHESIZING SAME

(75) Inventors: Thuy D. Dang, Centerville, OH (US); Matthew J. Dalton, Xenia, OH (US); Narayanan Venkatasubramanian, Beavercreek, OH (US); Joel A. Johnson, Xenia, OH (US); William A. Feld, Beavercreek, OH (US)

(73) Assignee: University of Dayton, Dayton, OH (US)

( * ) Notice: Subject to any disclaimer, the term of this patent is extended or adjusted under 35 U.S.C. 154(b) by 343 days.

(21) Appl. No.: 10/920,669

(22) Filed: Aug. 18, 2004

(65) Prior Publication Data

US 2005/0043449 A1    Feb. 24, 2005

Related U.S. Application Data

(60) Provisional application No. 60/495,955, filed on Aug. 18, 2003.

(51) Int. Cl.
*C08L 45/00* (2006.01)
*C08G 14/04* (2006.01)

(52) U.S. Cl. ............... 525/216; 525/290; 525/297; 525/219; 525/534; 525/255; 525/538; 524/136; 524/141; 528/125; 528/220

(58) Field of Classification Search ............... 525/216, 525/290, 297, 219, 534, 255, 538; 524/136, 524/141; 528/125, 220
See application file for complete search history.

(56) References Cited

U.S. PATENT DOCUMENTS

| 4,826,947 A | * | 5/1989 | Jansons et al. ............. 528/125 |
| 4,902,769 A | | 2/1990 | Cassidy et al. |
| 4,939,031 A | | 7/1990 | Torre et al. |
| 5,362,835 A | * | 11/1994 | Rolfe et al. ................. 528/87 |
| 5,876,856 A | | 3/1999 | Long |

* cited by examiner

*Primary Examiner*—James J. Seidleck
*Assistant Examiner*—Olga Asinovsky
(74) *Attorney, Agent, or Firm*—Dinsmore & Shohl LLP (57) ABSTRACT

Polyaryleneetherketone triphenylphosphine oxide compositions incorporating cycloaliphatic units are provided which may be used as a polymeric binders in thermal control coatings for use in space environments. A method is also provided for synthesizing the polyaryleneetherketone triphenylphosphine oxide compositions. A method is also provided for synthesizing the monomeric compositions used to make the polyaryleneetherketone triphenylphosphine oxide compositions.

8 Claims, 2 Drawing Sheets

FIG. 1

FIG.2. UV-Visible spectra of dilute solutions of the polymers in chloroform

POLYARYLENEETHERKETONE PHOSPHINE OXIDE COMPOSITIONS INCORPORATING CYCLOALIPHATIC UNITS FOR USE AS POLYMERIC BINDERS IN THERMAL CONTROL COATINGS AND METHOD FOR SYNTHESIZING SAME

CROSS REFERENCE TO RELATED APPLICATIONS

This application claims the benefit of provisional application Ser. No. 60/495,955 filed Aug. 18, 2003.

STATEMENT REGARDING FEDERALLY SPONSORED RESEARCH OR DEVELOPMENT

This invention was made with government support under Contract No. F33615-00-D-5008 awarded by the United States Air Force. The government has certain rights in the invention.

BACKGROUND OF THE INVENTION

This invention relates generally to thermal control coatings, and more particularly to polyaryleneetherketone phosphine oxide compositions incorporating cycloaliphatic units for use as polymeric binders in thermal control coatings and a method of synthesizing such compositions.

Spacecraft such as satellites and deep-space craft are exposed to a wide range of thermal conditions. The high intensity of direct solar radiation can potentially raise temperatures to dangerous levels. Thermal control of spacecraft is therefore important to reduce the absorption of solar radiation as well as dissipate internal heat to proper levels. Temperature control has currently been attained with the use of radiators having thermal control coatings on their surface. Such thermal control coatings typically comprise a potassium silicate binder pigmented with zinc oxide. This white coating exhibits a good initial diffuse reflectance for 380–1000 nm wavelength radiation and a moderate degradation in reflectance upon space environmental exposure. However, potassium silicate is a brittle inorganic glass with very poor flexibility and impact resistance, often showing failures due to film cracking. Another commercially available thermal control coating comprises a methyl silicone binder coating. However, while such a coating has good mechanical properties, it exhibits poor stability in space.

More recently, the use of certain polymers has been proposed for use as coatings in space environments. The use of polymers in thermal control coatings is desirable as they would provide significant weight reduction, good mechanical strength, and exhibit thermal and thermooxidative stability. However, in order to be used as thermal control coatings in space environments, such polymers must also be resistant to degradation by ultraviolet radiation and atomic oxygen.

Accordingly, there is a need in the art for polymers having improved resistance to UV radiation and atomic oxygen degradation which may be used in thermal control coatings.

SUMMARY OF THE INVENTION

The present invention meets that need by providing polyaryleneetherketone phosphine oxide compositions incorporating cycloaliphatic units which may be used as polymeric binders in thermal coatings for use in space applications. Methods for synthesizing such compositions are also provided.

The polymeric binders synthesized in accordance with the present invention have improved UV transparency and enhanced UV reflectance, reducing transfer of energy into unwanted heat. The polymeric binders may be used in thermal control coatings for use in low-earth-orbit satellite systems for the delivery of mobile satellite services.

According to one aspect of the present invention, a composition is provided having the formula where n is greater than 1.0.

According to another aspect of the invention, a composition is provided having the formula where n is greater than 1.0.

According to another aspect of the invention, a composition is provided having the formula where n is greater than 1.0.

According to yet another aspect of the invention, a composition is provided having the formula where n is greater than 1.0.

In another embodiment of the invention, a polymeric binder composition is provided comprising a composition containing an aryleneetherketone block, a triphenylphosphine oxide block, and a cycloaliphatic or cycloaliphatic cage-hydrocarbon structure. In one embodiment of the invention, the polymeric binder comprises a trans-1,4-cyclohexane-based polyaryleneetherketone triphenylphosphine oxide composition. In another embodiment, the polymeric binder comprises a 4,9-diamantane-based polyaryleneetherketone triphenylphosphine oxide composition. In yet another embodiment, the polymeric binder comprises a 1,3-adamantane-based polyaryleneetherketone triphenylphosphine oxide composition. In yet another embodiment, the polymeric binder comprises a 1,4-bicyclo(2.2.2)octane-based polyaryleneetherketone triphenylphosphine oxide composition.

In another embodiment of the invention, a thermal control coating is provided containing a polymeric binder comprising a composition containing an aryleneetherketone block, a triphenylphosphine oxide block, and a cycloaliphatic or cycloaliphatic cage-hydrocarbon structure. The polymeric binder may comprise a trans-1,4-cyclohexane-based polyaryleneetherketone triphenylphosphine oxide composition, a 4,9-diamantane-based polyaryleneetherketone triphenylphosphine oxide composition, a 1,3-adamantane-based polyaryleneetherketone triphenylphosphine oxide composition, or a 1,4-bicyclo(2.2.2)octane-based polyaryleneetherketone triphenylphosphine oxide composition.

The present invention also provides a method of synthesizing a polyaryleneetherketone triphenylphosphine oxide composition incorporating cycloaliphatic or cage hydrocarbon structural units which comprises displacing activated aromatic fluoro groups in 4,4'-difluorotriphenylphosphine oxide with bisphenoxide ions derived from a bis(4-hydroxybenzoyl) hydrocarbon monomer.

Preferably, the monomer is selected from the group consisting of trans-1,4-bis(4-hydroxybenzoyl)cyclohexane; 4,9-bis(4-hydroxybenzoyl)diamantane, 1,3-bis(r-hydroxybenzoyl)adamantane, and 1,4-bis(4-hydroxybenzoyl)bicyclo(2.2.2)octane.

In one embodiment, the synthetic route is wherein n is greater than 1.0.

In another embodiment, the synthetic route is wherein n is greater than 1.0.

In yet another embodiment, the synthetic route is where n is greater than 1.0.

In yet another embodiment, the synthetic route is wherein n is greater than 1.0.

Accordingly, it is a feature of the present invention to provide polyaryleneetherketone phosphine oxide compositions incorporating cycloaliphatic units for use as polymeric binders in thermal control coatings, and to a method for synthesizing the compositions. These, and other features and advantages of the present invention will become apparent from the following detailed description, the accompanying drawings, and the appended claims.

DETAILED DESCRIPTION OF THE PREFERRED EMBODIMENTS

Reference will now be made in detail to the preferred embodiments of the invention. In the synthesis of the polymeric binder of the present invention, three fundamental structures are used: an aryleneetherketone block, which imparts flexibility, processability and thermooxidative stability; a high temperature stable triphenylphosphine oxide block, which provides fire retardance and resistance to atomic oxygen in low earth orbit space environments; and a cycloaliphatic or cycloaliphatic cage-hydrocarbon structure for enhanced UV/visible transparency. This corresponds to the requirement of an absorption well below the solar absorption radiation maximum of 450 nm, as well as a desired overall UV reflectance due to little or no UV/visible absorptance in the 300–800 nm spectral range.

The present invention relates to the synthesis and characterization of a series of polyaryleneetherketone triphenylphosphine oxides incorporating a cycloaliphatic unit (trans-1,4-cyclohexylene) or cycloaliphatic cage-like structural units such as 1,3-adamantane-diyl and 4,9-diamantane-diyl moieties.

The present invention also relates to the synthesis of monomers trans-1,4-bis(4-hydroxybenzoyl)cyclohexane; 4,9-bis(4-hydroxybenzoyl)diamantane, and 1,3-bis(4-hydroxybenzoyl)adamantane. The respective cycloaliphatic diacid chloride, derived by the reaction of the corresponding diacid with excess thionyl chloride, may be reacted under Friedel-Crafts acylation conditions with anisole to yield the bis(4-methoxybenzoyl) compound which may be converted to the corresponding bis(4-hydroxybenzoyl) monomer by pyridine hydrochloride-mediated dealkylation.

The preparation of trans-1,4-bis(4-hydroxybenzoyl)cyclohexane is illustrated below.

The structures of the 4,9-diamantane and 1,-3-adamantane-based monomers synthesized in accordance with the present invention are shown below.

Polyaryleneetherketone triphenylphosphine oxides incorporating cycloaliphatic or cage hydrocarbon structural units may be synthesized by the nucleophilic displacement of the activated aromatic fluoro groups in 4,4'-difluorotriphenylphosphine oxide by the bisphenoxide ions derived from the bis(4-hydroxybenzoyl)hydrocarbon monomers described above. The polymerization reaction scheme for the preparation of the various polymers of the present invention is exemplified below for the trans-1,4-cyclohexane-based system.

The methodology described in this invention can also be applied to the preparation of other monomeric compositions, such as 1,4-bis(4-hydroxybenzoyl)bicyclo(2.2.2)octane, and the polyaryleneetherketone triphenylphosphine oxide composition derived from the monomer. The chemical structures of the monomer and polymer incorporating the bicycloaliphatic system are shown below.

Figure 1:
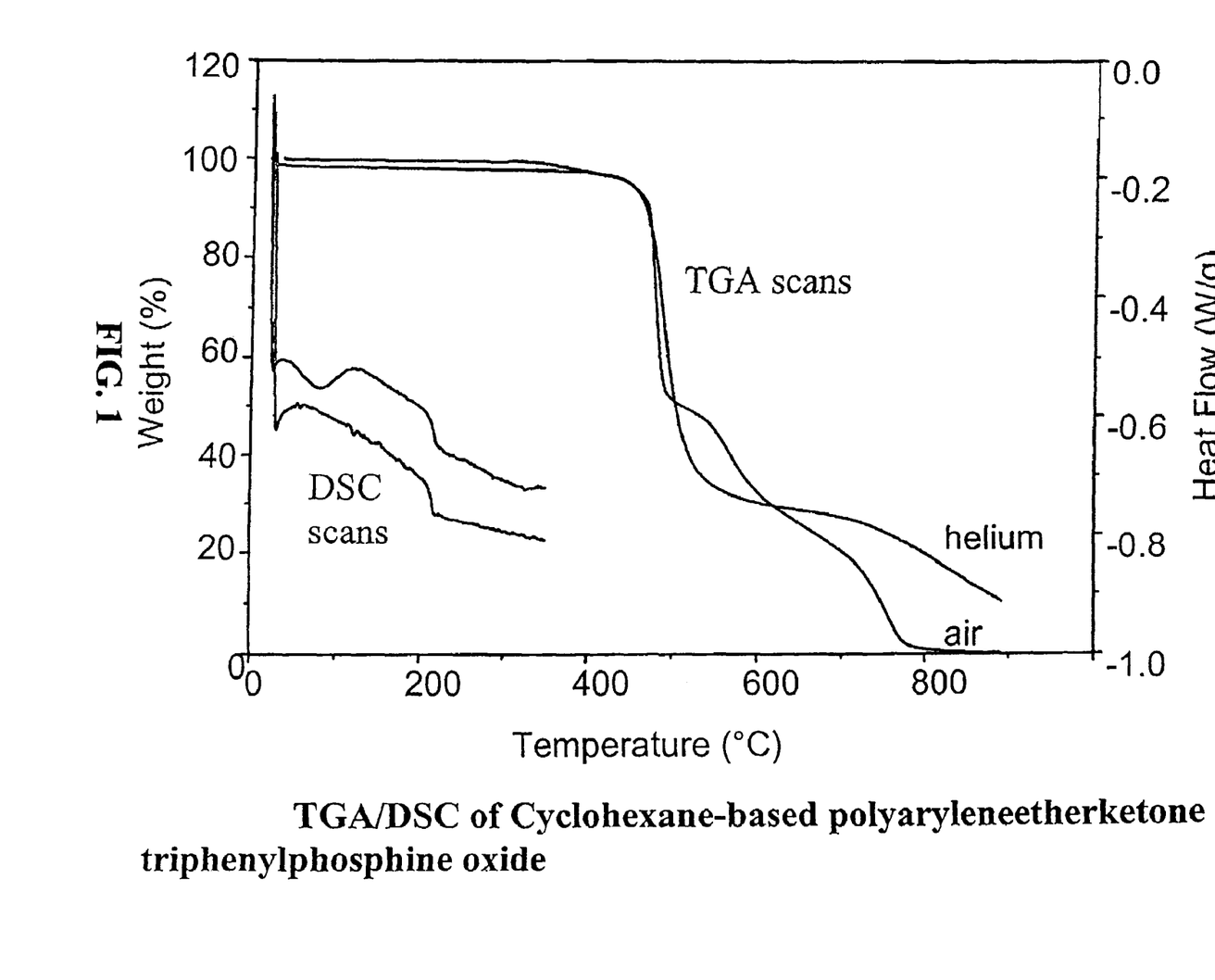
FIG. 1 is a graph illustrating the TGA and DSC analyses of cyclohexane-based polyaryleneetherketone triphenylphosphine oxide.
Figure 2:
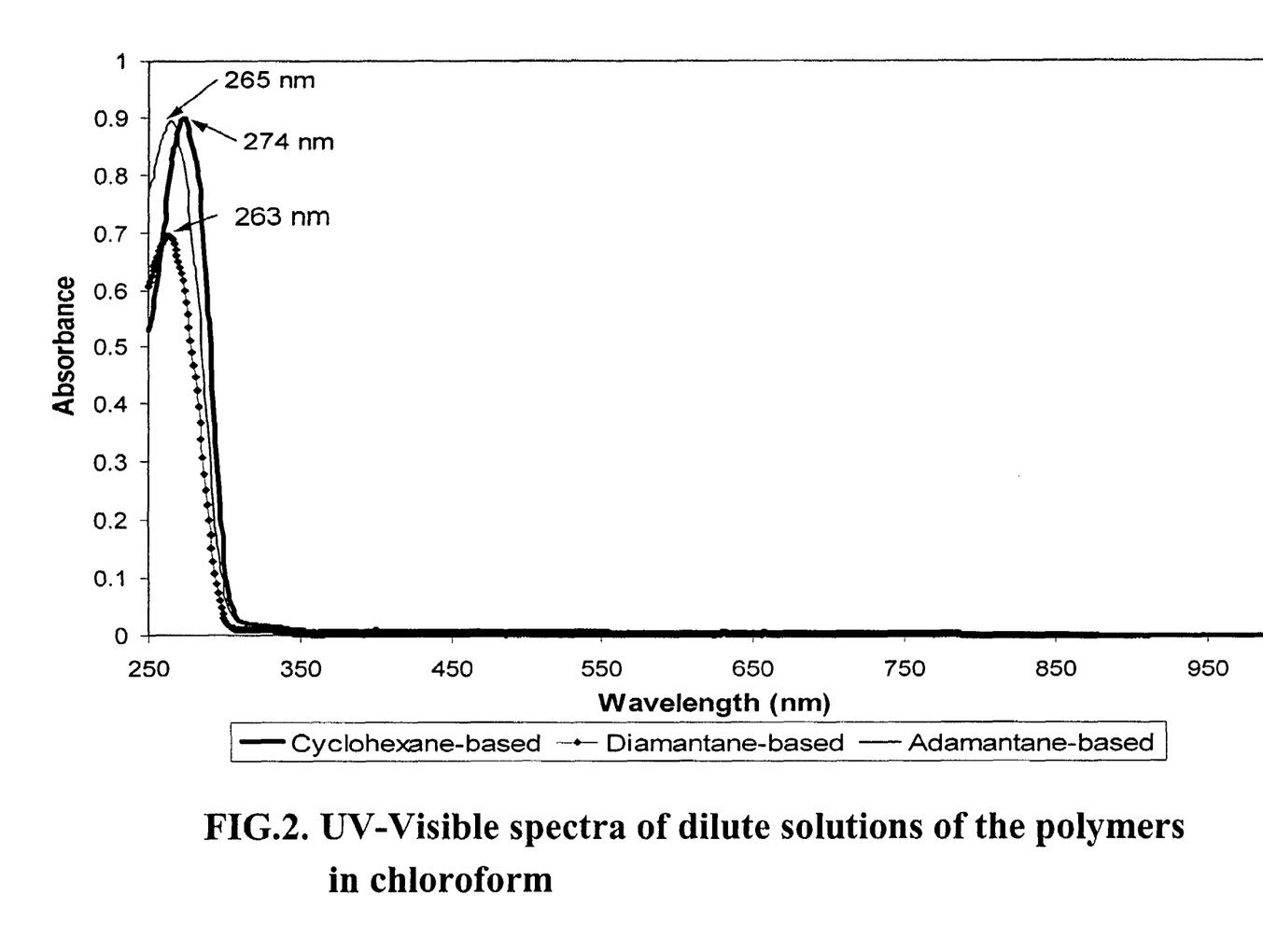
FIG. 2 is a graph illustrating the UV-visible spectra of dilute solutions of the polymers in chloroform.

The polymers obtained from this system have a high molecular weight as evidenced by their dilute solution viscosities in N,N-dimethylacetamide, and polymer films cast from chloroform are transparent, flexible and very tough. These high performance polymers are also suitable for high temperature use as indicated by their Tgs, which range from 192° C. to 239° C. The polymers also exhibit high thermal and thermooxidative stability as they have decomposition temperatures ranging from 468° C. for the cyclohexane-based polymer to 515° C. for the diamantane-based polymer, in TGA in a helium atmosphere, and 469° C.

to 493° C. in TGA in air. The solution properties and thermal and thermooxidative characteristics of these polymers are shown below in Table 1.

TABLE 1

| Polymer | Intrinsic Viscosity (dL/g, 30° C., DMAc)* | Solubility | Film Properties | $T_g$ (° C., DSC, $N_2$)** | TGA | |
|---|---|---|---|---|---|---|
| | | | | | $T_d$ (max, ° C., He)*** | $T_d$ (max, ° C., air)*** |
| cyclohexane-based | 1.18 | $CH_2Cl_2$, $CHCl_3$, DMAc, DMF | transparent, colorless, flexible, very tough | 215 | 468 | 469 |
| diamantane-based | 0.43 | $CH_2Cl_2$, $CHCl_3$, DMAc, DMF | transparent, colorless, flexible, very tough | 239 | 515 | 493 |
| adamantane-based | 0.38 | $CH_2Cl_2$, $CHCl_3$, DMAc, DMF | transparent, colorless, flexible, very tough | 192 | 510 | 491 |

*Initial concentration: 0.25 g/dL
**Rescan after heating to 250° C.
***Maximum weight loss for the temperature region In order that the invention may be more readily understood, reference is made to the following examples of compositions within the scope of the present invention, which examples are intended to be illustrative of the invention, but are not intended to be limiting in scope.

EXAMPLE 1

Materials 4,4'-Difluorotriphenylphosphine oxide was purchased from Daychem Laboratories, trans-1,4-cyclohexanedicarboxylic acid and 1,3-adamantanedicarboxylic acid were purchased from TCI America, and 4,9-diamantanedicarboxylic acid was acquired from Fluorochem, Inc. Thionyl chloride, anhydrous anisole, aluminum chloride, potassium carbonate, pyridine hydrochloride, N,N-dimethylacetamide (DMAc) and N-methylpyrrolidone (NMP) were purchased from Aldrich Co. All starting materials were used as received. All the synthesized monomers were characterized by melting point determination as well as by IR, NMR, mass spectral and elemental analyses.

Preparation of trans-1,4-bis(4-methoxybenzoyl)cyclohexane

A diacid chloride of trans-1,4-cyclohexanedicarboxylic acid was prepared by refluxing in thionyl chloride ($SOCl_2$) until a clear solution was obtained and then isolated by evaporation in vacuo. The crude product (6.33 g) was added slowly to a solution of $AlCl_3$ (9.7 g, 2.4 eq) and anhydrous anisole (33 g, 10 eq), chilled with an ice bath. The ice bath was removed and the reaction mixture was stirred overnight at room temperature under a nitrogen atmosphere. The thick orange mixture that resulted was precipitated in 0.1 M HCl and allowed to stir. The product was filtered, stirred in MeOH to remove traces of anisole, and the resulting fine white powder was vacuum-dried at 98° C. for 24 hours. The crude product was recrystallized from toluene to yield 9.52 g (89%) of the compound. (Melting point was 217–218° C.)

EXAMPLE 2

Preparation of trans-1,4-bis(4-hydroxybenzoyl)cyclohexane monomer

The dimethoxy compound from Example 1 (9.0 g) was reacted neat with pyridine hydrochloride (29.5 g, 10 eq) for 3 hours at 225° C. The reaction mixture was cooled to 100° C., precipitated in 0.1 M HCl, and the crude product was recrystallized from MeOH (melting point 260–263° C.). Yield of the off-white platelet-like crystals was 6.2 g, 75%.

EXAMPLE 3

Preparation of 4,9-bis(4-methoxybenzoyl)diamantane

The diacid chloride of 4,9-diamantanedicarboxylic acid was obtained by the reaction of the diacid with excess thionyl chloride under reflux conditions until a clear solution resulted. The solid was isolated by evaporation of the solvent in vacuo. The crude product (6.6 g, 0.0211 mole) was added slowly to a solution of $AlCl_3$ (6.75 g) and anhydrous anisole (22.8 g), chilled with an ice bath. The reaction mixture was stirred overnight at room temperature under a nitrogen atmosphere. The product was precipitated by pouring into aqueous HCl (0.1M) stirred and filtered. This was further stirred in methanol to remove anisole, and the resulting solid was recrystallized from about 700 ml toluene and 100 ml THF to yield 6.9 g (72%, melting point 213–214° C.).

EXAMPLE 4

Preparation of 4.9-bis(4-hydroxybenzoyl)diamantane monomer

In a round-bottomed flask fitted with a condenser, 4,9-bis(4-methoxybenzoyl)-diamantane (13.0 g, 0.0285 mole) was demethylated by heating with excess pyridine hydrochloride (33 g, 0.2850 mole) to 225° C. for three hours and the mixture was cooled. The product was precipitated in 40 ml concentrated HCl diluted with 200 ml water. The resulting solid was filtered and dried. The crude product was dissolved in tetrahydrofuran (THF) and hexane was added to the hot THF solution until the solution became slightly turbid. The solution was then slowly cooled to obtain crystals of the monomer (melting point 313–315° C.). Isolated yield was 7.0 g (57%).

EXAMPLE 5

Preparation of 1,3-bis(4-methoxybenzoyl)adamantane 1,3-Adamantanedicarboxylic acid (10.0 g) was converted into its diacid chloride by refluxing with 40 ml thionyl chloride. The acid chloride was obtained by evaporating off excess thionyl chloride. The diacid chloride (0.0438 mole, 11.45 g) was added slowly to a solution of $AlCl_3$ (14.03 g, 0.1052 mole) in anhydrous anisole (47.41 g, 0.4384 mole), chilled with an ice bath. The reaction mixture was stirred overnight at room temperature under a nitrogen atmosphere. The mixture was worked up in about 400 ml of 0.2 M HCl, filtered and stirred in methanol to precipitate a crude white solid. The solid was recrystallized from toluene to yield 11.6 grams of the crystals (66%, melting point 148–150° C.).

EXAMPLE 6

Preparation of 1,3-bis(4-hydroxybenzoyl)adamantane monomer 11.0 g (0.0272 mole) of 1,3-bis(4-methoxybenzoyl)adamantane was placed in a 250 ml round-bottomed flask fitted with a reflux condenser, along with 31.5 g (0.272 mole) of pyridine hydrochloride. The slurry was heated to 225° C. for three hours and the product was precipitated in 40 ml concentrated HCl diluted with 200 ml water. The solid was filtered and dried. The solid was recrystallized from ethyl acetate. The isolated yield of the purified compound was 6.6 g (64%, melting point 208–209° C.).

EXAMPLE 7

Preparation of trans-1,4-cyclohexane-based polyaryleneetherketone triphenylphosphine oxide A mixture of trans-1,4-bis(4-hydroxybenzoyl)cyclohexane (1.2975 g), 4,4'-difluorotriphenylphosphine oxide (1.2571 g) and potassium carbonate (1.33 g, 2.4 eq) was added to a 100 ml three-neck round bottom flask equipped with a mechanical stirrer, nitrogen inlet/outlet, and a Dean-Stark trap. N-methylpyrrolidone (NMP, 16 ml) and toluene (about 30 ml) were added and the reaction mixture was allowed to reflux with stirring for at least 4 hours. Water was azeotroped off, and the temperature was raised to maintain reflux. After an hour, some of the NMP was collected in the Dean-Stark trap to remove any residual water and achieve a final concentration of 15% by weight. The polymerization was run at reflux temperature (about 215° C.) in NMP for 3 hours and was cooled to about 100° C. before precipitation into 400 ml of 50/50 MeOH/acetic acid (HOAc). The stringy solid was shredded in a blender and soxhlet-extracted with water, and then dried in a drying pistol at 100° C. under vacuum for 24 hours. The yield of the off-white polymer was 2.47 g (98%). The intrinsic viscosity of the polymer, measured in N,N-dimethylacetamide (DMAc) at 30° C. for an initial concentration of 0.25 g/dl, was 1.18. The polymer was redissolved in chloroform and reprecipitated in heptane. After filtration, the polymer was again vacuum dried at 100° C., and then cast into transparent, tough and flexible films of various thicknesses from the chloroform solutions.

EXAMPLE 8

Preparation of 4,9-diamantane-based polyaryleneetherketone triphenylphosphine oxide A mixture of 4,9-bis(4-hydroxybenzoyl) diamantane (1.3212 g) and 4,4'-difluorotriphenylphosphine oxide (0.9689 g) and potassium carbonate (1.022 g, 2.4 equivalents) was added to a 100 mL three-neck round-bottom flask equipped with a mechanical stirrer, nitrogen inlet/outlet, and a Dean-Stark trap filled with dry toluene. DMAc (7.2 ml) and toluene (15 ml) were added and the reaction mixture was allowed to reflux with stirring for at least 4 hours. After removal of the azeotrope and excess toluene, the temperature was raised to 165° C. and the polymerization was allowed to proceed for 16 hours at the reflux temperature of DMAc. The calculated final polymer concentration was about 23 wt %. The polymer was precipitated in water, shredded in a blender and filtered. The solid was dried under vacuum for 24 hours at 100° C. 1.98 g of the polymer was isolated (92% yield). The intrinsic viscosity of the polymer, measured in DMAc at 30° C., was 0.27 dl/g for an initial polymer concentration of 0.0632 g/25 ml.

EXAMPLE 9

Preparation of 4,9-diamantane-based polyaryleneetherketone triphenylphosphine oxide A mixture of 4,9-bis(4-hydroxybenzoyl)diamantane (1.3212 g), 4,4'-difluorotriphenylphosphine oxide (0.9689 g) and potassium carbonate (1.022 g, 2.4 equivalents) was added to a 100 mL three-neck round-bottom flask equipped with a mechanical stirrer, nitrogen inlet/outlet, and a Dean-Stark trap filled with dry toluene. NMP (7.2 ml) and toluene (15 ml) were added and the reaction mixture was allowed to reflux with stirring for at least 4 hours. After removal of the azeotrope and excess toluene, the polymerization was run for 16 hours at 165° C. The calculated final polymer concentration was about 23 wt %. The polymer was precipitated in water, shredded in a blender, and filtered. The solid was dried under vacuum for 24 hours at 100° C. The isolated yield of the polymer was 2.05 g (95%). The intrinsic viscosity of the polymer, measured in DMAc at 30° C., was 0.31 dl/g for an initial polymer concentration of 0.0625 g/25 ml.

EXAMPLE 10

Preparation of 4,9-diamantane-based polyaryleneetherketone triphenylphosphine oxide A mixture of 4,9-bis(4-hydroxybenzoyl)diamantane (2.5711 g, $6 \times 10^{-3}$ mole) and 4,4'-difluorotriphenylphosphine oxide (1.8856 g, $6 \times 10^{-3}$ mole) and potassium carbonate (1.99 g, $14.4 \times 10^{-3}$ moles) was added to a 100 mL, three-neck round-bottom flask equipped with a mechanical stirrer, nitrogen inlet/outlet, and a Dean-Stark trap. N-methylpyrrolidone (NMP, 23 ml) and toluene (about 50 ml) were added and the reaction mixture was allowed to reflux with stirring for at least 4 hours. After removal of the azeotrope and excess toluene, the reaction temperature was raised to 215° C. and the polymerization was run for about 5 hours. The calculated final polymer concentration was about 15 wt %. The mixture was cooled to about 100° C. before precipitation into 500 ml of 50/50 MeOH/HOAc. The stringy solid was shredded in a blender, soxhlet-extracted with water, and then dried in a drying pistol at 100° C. under vauum for 24 hours. The isolated yield of the polymer was 3.89 g (about 93%). The intrinsic viscosity of the polymer, measured in N,N-dimethylacetamide (DMAc) at 30° C. for an initial concentration of 0.25 g/dl, was 0.43. The polymer was redissolved in chloroform, treated with activated charcoal for 15 minutes and filtered. The polymer was reprecipitated in heptane and the filtered polymer was dried in a drying pistol at 100° C. under vacuum overnight. Elemental analysis of the polymer sample for $C_{46}H_{39}O_5P$ showed the following, calculated: C, 78.61; H, 5.60; P, 4.41; O, 11.38. found: C, 77.23; H, 5.48; P, 4.10; O, 11.10. 0.03 g of the polymer was redissolved in 10 ml chloroform and a transparent, tough, flexible polymer thin film (about 5µ thick) was cast from the filtered polymer solution by evaporating the solvent from a flat casting dish. FT-IR spectrum of the polymer thin film was corroborative of the expected chemical structure of the polymer. The spectral features are indicative of an aromatic C—H stretch at 3058 $cm^{-1}$, the distinct diamantane secondary and tertiary C—H stretching frequencies at 2918 and 2874 $cm^{-1}$, an intense carbonyl stretch at 1667 $cm^{-1}$ due to the aryl adamantyl ketone group, a strong aromatic C=C at 1587 $cm^{-1}$, a very intense asymmetric —C—O—C— stretch at 1241 $cm^{-1}$ due to the diphenylether linkage and a strong P=O stretch at 1170 $cm^{-1}$ due to the arylphosphine oxide unit.

EXAMPLE 11

Preparation of 1,3-adamantane-based polyaryleneetherketone triphenylphosphine oxide A mixture of 1,3-bis(4-hydroxybenzoyl)adamantane (2.2589 g, $6 \times 10^{-3}$ mole) and 4,4'-difluorotriphenylphosphine oxide (1.8856 g, $6 \times 10^{-3}$ mole) and potassium carbonate (1.99 g, $14.4 \times 10^{-3}$ mole) was added to a 100 mL, three-neck round-bottom flask equipped with a mechanical stirrer, nitrogen inlet/outlet, and a Dean-Stark trap. N-methylpyrrolidone (NMP, 23 ml) and toluene (about 50 ml) were added and the reaction mixture was allowed to reflux with stirring for at least 4 hours. After removal of the azeotrope and excess toluene, the reaction temperature was raised to 215° C. and the polymerization was run for about 3.5 hours. The mixture was cooled to about 100° C. before precipitation into 500 ml of 50/50 MeOH/HOAc. The stringy solid was shredded in a blender, soxhlet-extracted with water, and then dried in a drying pistol at 100° C. under vacuum for 24 hours. The isolated yield of the polymer was 3.7 g (about 95%). The intrinsic viscosity of the polymer, measured in N,N-dimethylacetamide (DMAc) at 30° C. for an initial concentration of 0.25 g/dl, was 0.38. A transparent, tough, flexible polymer film was cast from the filtered polymer solution in chloroform by evaporating the solvent from a flat casting dish.

In the foregoing specification, the invention has been described with reference to specific embodiments. However, one of ordinary skill in the art appreciates that various modifications and changes can be made without departing from the skill of the present invention as set forth in the claims below. Accordingly, the specification and figures are to be regarded in an illustrative rather than a restrictive sense, and all such modifications are intended to be included within the scope of the present invention.

What is claimed is:

1. A polymeric binder composition comprising a composition containing an aryleneetherketone block, a triphenylphosphine oxide block, and a cycloaliphatic or cycloaliphatic cage-hydrocarbon structure.

2. The polymeric binder of claim 1 comprising a trans-1,4-cyclohexane-based polyaryleneetherketone triphenylphosphine oxide composition.

3. The polymeric binder of claim 1 comprising a 4,9-diamantane-based polyaryleneetherketone triphenylphosphine oxide composition.

4. The polymeric binder of claim 1 comprising a 1,3-adamantane-based polyaryleneetherketone triphenylphosphine oxide composition.

5. The polymeric binder of claim 1 comprising a 1,4-bicyclo(2.2.2)octane-based polyaryleneetherketone triphenylphosphine oxide composition.

6. A monomer comprising trans-1,4-bis(4-hydroxybenzoyl)cyclohexane.

7. A monomer comprising 4,9-bis(4-hydroxybenzoyl)diamantane.

8. A monomer comprising 1,3-bis(4-hydroxybenzoyl)adamantane.

* * * * *